United States Patent
Hines et al.

(10) Patent No.: US 7,815,609 B2
(45) Date of Patent: Oct. 19, 2010

(54) DISPOSABLE INFUSION DEVICE POSITIVE PRESSURE FILLING APPARATUS AND METHOD

(75) Inventors: Craig Hines, San Francisco, CA (US); Cory Williamson, Austin, TX (US)

(73) Assignee: Calibra Medical, Inc., Redwood City, CA (US)

( * ) Notice: Subject to any disclaimer, the term of this patent is extended or adjusted under 35 U.S.C. 154(b) by 45 days.

(21) Appl. No.: 12/004,477

(22) Filed: Dec. 19, 2007

(65) Prior Publication Data

US 2009/0163865 A1 Jun. 25, 2009

(51) Int. Cl.
*A61M 5/32* (2006.01)
(52) U.S. Cl. .............................. 604/180; 604/48; 604/38
(58) Field of Classification Search .................... 604/38, 604/152, 180, 890.1, 131
See application file for complete search history.

(56) References Cited

U.S. PATENT DOCUMENTS

| 4,714,462 A | 12/1987 | Didomenico |
| 5,197,322 A | 3/1993 | Indravudh |
| 5,776,103 A | 7/1998 | Kriesel et al. |
| 6,355,019 B1 * | 3/2002 | Kriesel et al. ............... 604/132 |
| 2007/0282269 A1 * | 12/2007 | Carter et al. ........... 604/164.01 |

OTHER PUBLICATIONS

International Search Report for PCT Application PCT/US2008/087215 dated Jun. 12, 2009, conducted by Korean Intellectual Property Office.

* cited by examiner

*Primary Examiner*—Nicholas D Lucchesi
*Assistant Examiner*—Leah Stohr
(74) *Attorney, Agent, or Firm*—Richard O. Gray, Jr.; Graybeal Jackson LLP

(57) ABSTRACT

An infusion system comprises a disposable wearable infusion device having a body arranged to be adhered to a patient's skin and a reservoir for holding a liquid medicament to be infused into the patient. The infusion system further comprises a filler device arranged to be detachably received by the infusion device and to provide a positive pressure directly to the liquid medicament to transfer a volume of the liquid medicament to the infusion device reservoir.

4 Claims, 4 Drawing Sheets

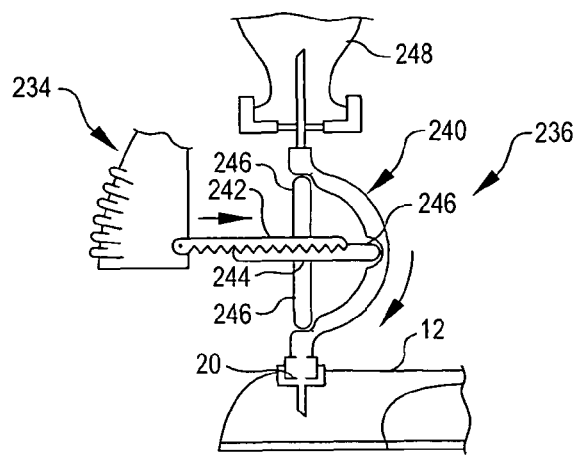
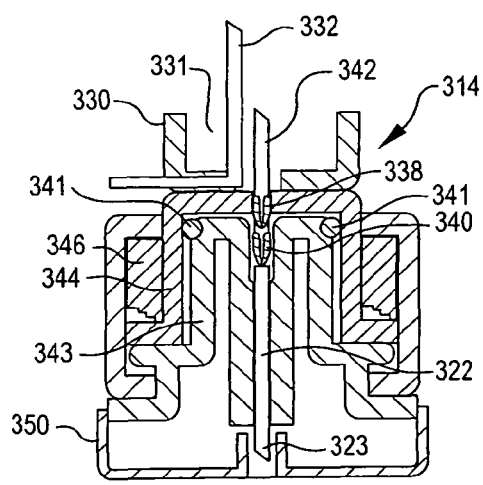
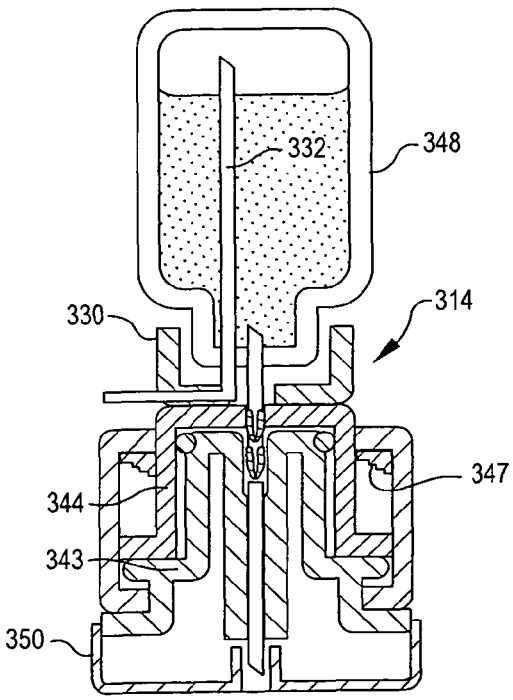

DISPOSABLE INFUSION DEVICE POSITIVE PRESSURE FILLING APPARATUS AND METHOD

BACKGROUND OF THE INVENTION

Tight control over the delivery of insulin in both type I diabetes (usually juvenile onset) and type II diabetes (usually late adult onset), has been shown to improve the quality of life as well as the general health of these patients. Insulin delivery has been dominated by subcutaneous injections of both long acting insulin to cover the basal needs of the patient and by short acting insulin to compensate for meals and snacks. Recently, the development of electronic, external insulin infusion pumps has allowed the continuous infusion of fast acting insulin for the maintenance of the basal needs as well as the compensatory doses (boluses) for meals and snacks. These infusion systems have shown to improve control of blood glucose levels. However, they suffer the drawbacks of size, cost, and complexity. For example, these pumps are electronically controlled and must be programmed to supply the desired amounts of basal and bolus insulin. This prevents many patients from accepting this technology over the standard subcutaneous injections.

Hence, there is a need in the art for a convenient form of insulin treatment which does not require significant programming or technical skills to implement to service both basal and bolus needs. Preferably, such a treatment would be carried out by an infusion device that is simple to use and mechanically driven negating the need for batteries and the like. It would also be preferable if the infusion device could be directly attached to the body and not require any electronics to program the delivery rates. The insulin is preferably delivered through a small, thin-walled tubing (cannula) through the skin into the subcutaneous tissue similar to technologies in the prior art.

While the idea of such a simple insulin delivery device is compelling, many obstacles must be overcome before such a device may become a practical realty. One problem resides in insulin supply. Patients vary greatly on the amount of insulin their device must carry to provide treatment over a fixed time period of, for example, three days. This is one environment where one size does not fit all. Another problem is with cannula deployment to support insulin delivery. Cannula deployment to support delivery of the insulin beneath the patient's skin must be made easy and convenient. This is not as easy as it seems because cannula deployment, as generally and currently performed in the art, requires insertion of a cannula carrying needle into the patient and then retraction of only the needle to leave the cannula in place beneath the patient's skin.

Still further, medical devices, such as IV pumps, insulin pumps and the like, designed to deliver liquid medicaments to patients by means of intravascular, intramuscular or interstitial injection are subject to problems due to difficulties in filling with the medicament prior to use. Specifically, the process of transferring a liquid medicament from a storage vial to the drug delivery device can be both difficult and error prone. The difficulty can be caused by the need to maintain sterility of the contacting surfaces, and the logistics of using an intermediate transfer device such as a syringe. Errors can be caused by miss-measurement of fluids and by the inadvertent introduction of air into the drug delivery device. While the difficulties can be inconvenient, the errors can result in more serious problems such miss-dosing. The consequences of incorrect treatment due to miss-dosing can vary from minor to serious. In the case of insulin delivery, incorrect dosing can lead to acute hypoglycemia or chronic hyperglycemia.

One currently proposed method of preparing a disposable insulin delivery device for use includes transferring insulin from a liquid medicament vial to the insulin delivery device. As proposed, this may be accomplished with a syringe and mounted needle by first drawing an amount of air into the syringe equal to the amount of insulin that will be withdrawn from the vial. Next, the vial septum is pierced with the needle and air is injected from the syringe into the vial, thus pressurizing the vial. The desired amount of insulin is then withdrawn from the vial into the syringe and thereafter, the needle is withdrawn from the vial. Next, the syringe is held in a vertical orientation to allow entrapped air to rise to the top. The syringe plunger is then gently advanced until the air has been ejected and a small amount of fluid is expressed from the syringe. The septum on the medicament delivery device is then pierced with the syringe to access the device reservoir and the insulin is injected into the reservoir. Lastly, the reservoir is inspected for air bubbles and those larger than 1 mm in diameter are removed by reinserting the syringe needle and aspirating the bubble.

This foregoing procedure is subject to error during the syringe filling and degassing steps, and during the reservoir filling step. Error during either step can result in excess air injected into the medicament delivery device. Excess air in the reservoir of the medicament delivery device can adversely affect the amount of insulin delivered to the patient during use, thereby compromising treatment.

Hence, there is a need for an improved filling device and method that will reduce the complications and potential errors associated with transferring a medicament from a storage vial to a drug delivery device. As will be seen subsequently, the present invention addresses these and other issues.

SUMMARY OF THE INVENTION

In one embodiment the invention provides an infusion system comprising a disposable wearable infusion device having a body arranged to be adhered to a patient's skin and a reservoir for holding a liquid medicament to be infused into the patient. The system further comprises a filler device arranged to be detachably received by the infusion device and to provide a positive pressure directly to the liquid medicament to transfer a volume of the liquid medicament to the infusion device reservoir.

The filler device may be arranged to receive a vial of the liquid medicament. The filler device may be arranged to transfer a set volume of the liquid medicament from the vial to the infusion device reservoir. The filler may further include a chamber that receives the liquid medicament from the vial before the liquid medicament is transferred to the infusion device reservoir.

The filler may include a piston and a piston chamber to meter a predetermined volume of the medicament to the reservoir. Alternatively, the filler may include a peristaltic pump. The filler may further include a vent that vents the liquid medicament to atmospheric pressure.

In another embodiment, the invention provides a method comprising the steps of providing a disposable infusion device adapted to adhere to a patient's skin and having a reservoir for holding a liquid medicament to be infused into the patient, coupling a medicament filler to the infusion device reservoir, and filling the infusion device reservoir with the liquid medicament. The reservoir may be filled by providing a positive pressure with the medicament filler directly to the medicament.

The coupling step may comprise detachably joining the medicament filler to the infusion device. The filling step may further comprise providing the medicament filler with a vial of the liquid medicament. The method may comprise the further step of venting the liquid medicament to atmospheric pressure. The method may comprise the further step of transferring the liquid medicament to an intermediate chamber before transferring the liquid medicament to the infusion device reservoir.

The filling step may include providing a piston and a piston chamber, filling the piston chamber with the liquid medicament, and causing the piston to act upon the liquid medicament within the piston chamber.

In a further embodiment, the invention provides a filler device for filling a reservoir of a disposable wearable infusion device with a liquid medicament. The filler device comprises an outlet arranged to be detachably received by the infusion device and a pump that provides a positive pressure directly to the liquid medicament to transfer a volume of the liquid medicament to the infusion device reservoir.

The device may further comprises a device body defining a cavity, and the cavity may be arranged to receive a vial of the liquid medicament. The filler device may be further arranged to transfer a set volume of the liquid medicament from the vial to the infusion device reservoir.

The pump may comprise a piston and a piston chamber. The piston may act upon the liquid medicament within the piston chamber to meter a predetermined volume of the liquid medicament to the reservoir.

Alternatively, the pump may be a peristaltic pump. The device may further comprise a vent that vents the liquid medicament to atmospheric pressure. The device may further comprise a chamber that receives the liquid medicament before the liquid medicament is transferred to the infusion device reservoir.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 5 is side view illustrating details of the filling apparatus FIG. 4;

FIG. 6 is a sectional side view of a medicament filling apparatus according to a still further embodiment of the present invention;

FIG. 7 is a sectional side view illustrating the apparatus of FIG. 6 after receiving a vial of liquid medicament;

DETAILED DESCRIPTION OF THE INVENTION

Figure 1:
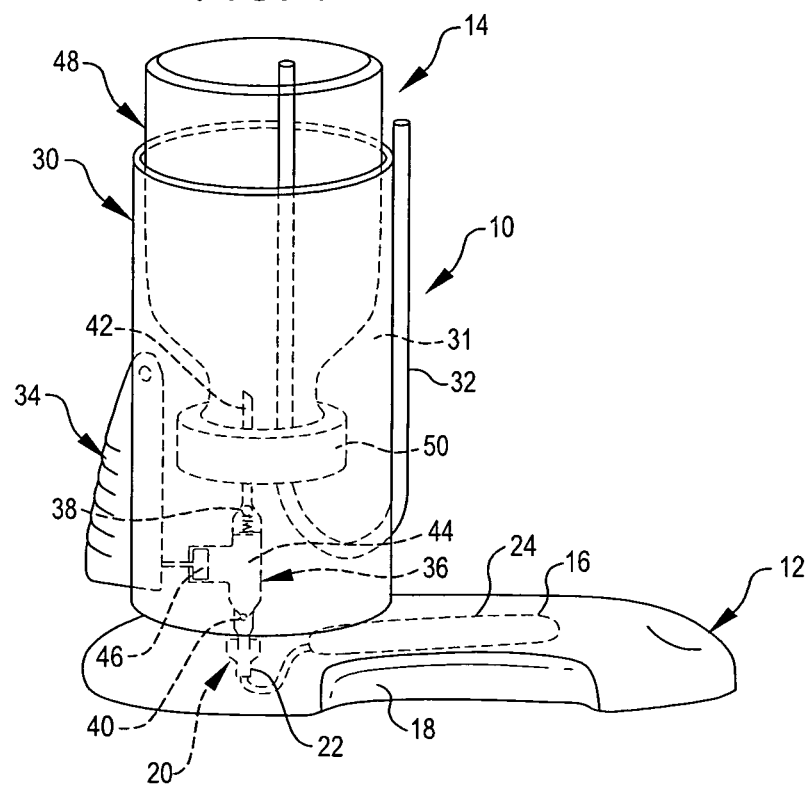
FIG. 1 is a perspective view of an infusion system including a medicament filling apparatus according to a first embodiment of the present invention.

Referring now to FIG. 1, it is a perspective view of an infusion system 10 according to a first embodiment of the present invention. The system 10 generally comprises a wearable disposable infusion device 12 and a liquid medicament filling device 14.

The infusion device 12 generally includes a housing 16, at least one actuator button 18, a fill port 20, and a reservoir 24. The device is preferably arranged to receive a cannula (not shown) after it is filled with liquid medicament, such as insulin, to be administered to the wearer of the device 12. The actuator button 18 may be one of two actuator buttons which require concurrent actuation to cause the liquid medicament to be delivered. This arrangement helps to prevent accidental dosing. The fill port 20 may include a septum (not shown) that may be pierced by a needle 22 carried by the filling device 14 during the filling of device reservoir 24. This serves to promote sterility during the filling process. To these and other ends, the infusion device may take a form as shown, and described, for example, in U.S. application Ser. No. 11/604,166, filed Nov. 22, 2006 for DISPOSABLE INFUSION DEVICE FILLING APPARATUS AND METHOD, which application is owned by the assignee of the present invention and incorporated herein by reference in its entirety.

The filling device 14 generally includes a generally cylindrical housing 30, a vent tube 32, an actuator 34, and a metering pump 36. The metering pump 36 includes a first one-way valve 38, a second one-way valve 40, a needle 42, a piston chamber 44, and a piston 46.

The housing 30 has a cavity 31 dimensioned to receive a vial 48 containing the insulin or other liquid medicament. When the vial 48 is received within the housing 30, the end cap 50 of the vial 48 is pierced first by the vent tube 32 and then by the needle 42. The length of the vent tube 32 is selected so that when the vial 48 is fully received within the housing 30, the end of the vent tube 32 extends above the liquid medicament. The vent tube 32 thus permits the liquid medicament to flow freely from the vial 48, through the one-way valve 38, and into the chamber 44 of the metering pump 36.

Figure 2:
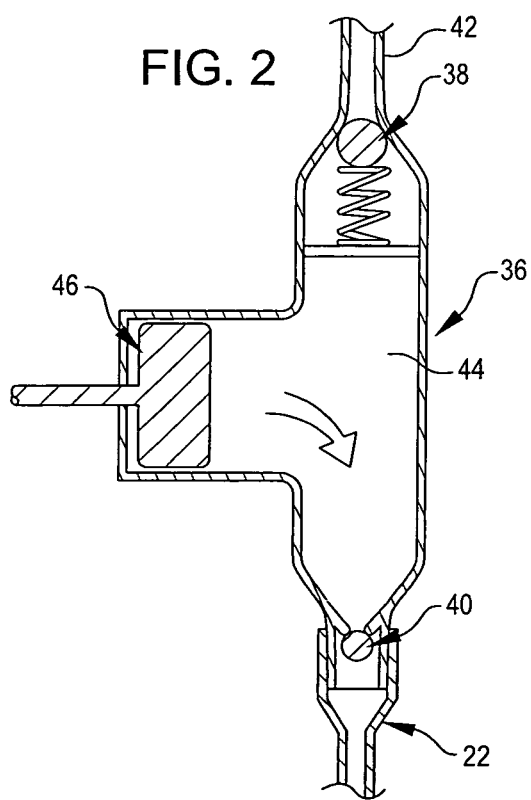
FIG. 2 is a sectional side view illustrating details of the filling apparatus of FIG. 1.

The metering pump 36 is shown in greater detail in FIG. 2. When the actuator 34 is depressed, the piston 46 is caused to exert a direct positive pressure on the liquid medicament within the piston chamber 44 to displace a set volume or known quantity of the liquid medicament from the piston chamber 44. The set volume or known quantity of displaced liquid medicament flows through the one-way valve 40, and through the needle 22 into the reservoir 24. Hence, the number of times that the actuator 36 is depressed determines the amount of liquid medicament transferred form the vial 48 to the reservoir 24 of the device 12. This enables the reservoir 24 to be filled with a precise and desired amount liquid medicament. The valve 40 is preferably a drip-less, excellent flow, low volume valve. To that end, the valve 40 may be a swabable luer valve of the type known in the valve art.

In use, the needle 22 is attached to the one-way valve 40 of the metering pump 36. Next, the vial 48 of liquid medicament is placed in the housing 30 and the filling device 14 is releaseably joined with the infusion device 12. Next, the actuator 34 is depressed the number of times required to transfer the desired quantity of the liquid medicament from the vial to the fill port 20 and thus the reservoir 24 of the infusion device 12. When the desired quantity of liquid medicament has been transferred to the device 12, the filling device 14 is removed from the infusion device 12, the needle 22 is removed from the one-way valve 22, and the filling device 14 is placed in sterile storage with the vial 48 remaining in the housing 30. Such storage supports multiple use of the filling device.

Figure 3:
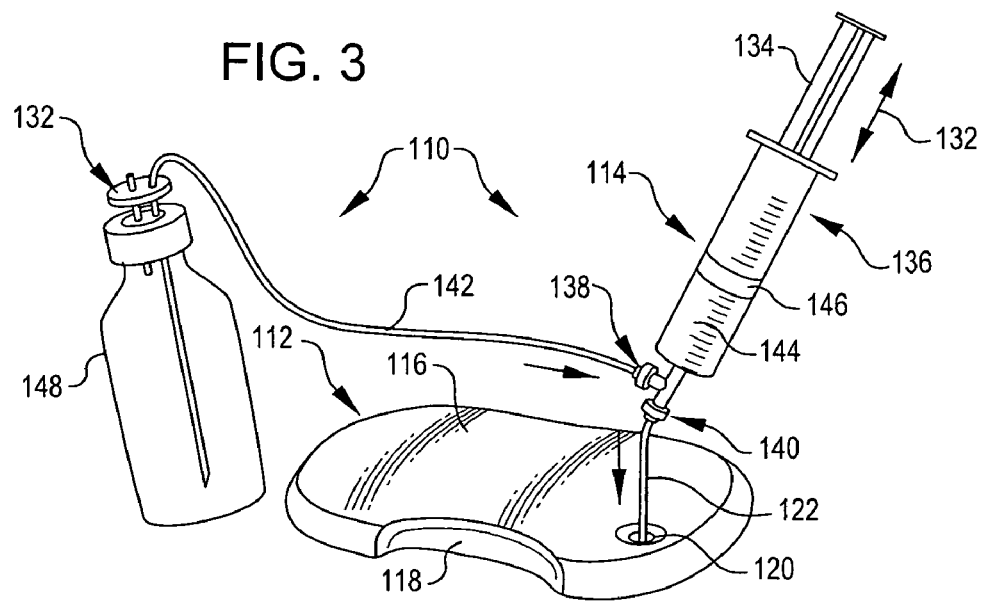
FIG. 3 is a perspective view of an infusion system and medicament filling apparatus according to a second embodiment of the present invention.

FIG. 3 is a perspective view of an infusion system 110 comprising an infusion device 112 and a medicament filling device 114 according to a second embodiment of the present invention. As in the previous embodiment, the infusion device 112 generally includes a housing 116, at least one actuator button 118, a fill port 120, and a reservoir (not shown). The device is preferably arranged to receive a cannula (not shown) after it is filled with liquid medicament, such as insulin, to be administered to the wearer of the device 112. The actuator button 118 may again be one of two actuator buttons which require concurrent actuation to cause the liquid medicament to be delivered. As before, this arrangement helps to prevent accidental dosing. The fill port 120 may be dimensioned to receive a fill tube 122 carried by the filling device 114 during the filling of device reservoir.

The filling device 114 includes a syringe 136, a first one-way valve 138, a second one-way valve 140, and a transfer tube 142. The transfer tube 142 couples the interior of the vial 148 to the one-way vale 138. This permits the liquid medicament to be drawn from the vial 148 as the piston 144 of the syringe 136 is withdrawn through movement of the actuator 134. The actuator movement is represented by arrows 132. As the piston 146 is withdrawn, a chamber 144 is formed of a known volume that is filled with the liquid medicament. The medicament may flow freely due to the vacuum release or vent tube 132.

When the chamber 144 is expanded to hold a desired or set volume of the liquid medicament, the actuator 134 is moved in the other direction to cause the piston 146 to exert a direct positive pressure on the liquid medicament. The liquid medicament thus flows from the syringe chamber 144 through the fill tube 122 and into the fill port 120 of the device 112. When the volume of the chamber 144 has been diminished completely, the known or set volume of liquid medicament has been transferred to the device 112.

Figure 4:
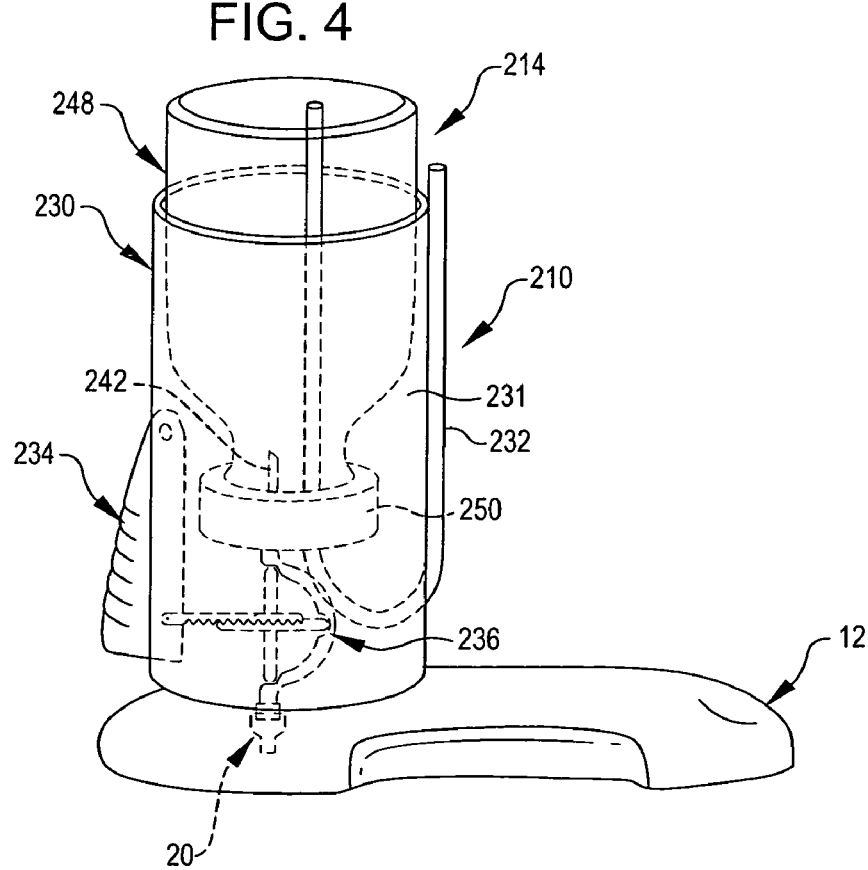
FIG. 4 is a perspective view of an infusion system and medicament filling apparatus according to a further embodiment of the present invention.

FIG. 4 is a perspective view of an infusion system 210 and medicament filling device 214 according to a further embodiment of the present invention. The system 210 may include the infusion device 12 of the embodiment of FIG. 1, previously described.

The filling device 214 generally includes a generally cylindrical housing 230, a vent tube 232, an actuator 234, and a metering pump 236. The metering pump 236 is in the form of a peristaltic pump.

The housing 230 has a cavity 231 dimensioned to receive a vial 248 containing the insulin or other liquid medicament. When the vial 248 is received within the housing 230, the end cap 250 of the vial 248 is pierced first by the vent tube 232 and then by the needle 242. Again, the length of the vent tube 232 is selected so that when the vial 248 is fully received within the housing 230, the end of the vent tube 232 extends above the liquid medicament. The vent tube 232 thus vents the vial to atmospheric pressure to permit the liquid medicament to flow freely from the vial 248.

The peristaltic metering pump 236 is shown in greater detail in FIG. 5. Here it may be seen that the peristaltic pump 236 includes a plurality of radially extending rotating fingers 246. The fingers 246 rotate about a toothed hub 244. The teeth of the toothed hub 244 are driven by the teeth of a toothed drive member 242 connected to the actuator 234. A transfer tube 240 conducts the liquid medicament from the vial 248 to the fill port 20 of the device 12. The fingers 246 are rotated when the actuator 234 is depressed. The ends of the rotating fingers engage the transfer tube 240 to push the liquid medicament long to the fill port 20. Each depression of the actuator 234 meters a set volume of the liquid medicament to the fill port 20. Hence again, the number of actuator depressions determines with precision the volume of liquid medicament transferred to the fill port 20. Also, in this embodiment, the liquid medicament, although receiving direct positive pressure from the peristaltic pump, is never actually touched by pump mechanism.

FIGS. 6-9 show a medicament filling apparatus 314 according to a still further embodiment of the present invention. As shown on FIG. 6, the device 314 includes a plunger 344 that reciprocates on a frame 343. Seal rings 341 provide a seal between the plunger 344 and the frame 343. On top of the plunger 344 is a ring 330 that defines a cavity 331 for receiving a vial of liquid medicament. The device 314 also includes a vent tube 332 and a transfer tube 342. One-way valve 338, as will be seen subsequently, permits the liquid medicament to be transferred to an intermediate chamber when the plunger 344 is withdrawn. Another one-way valve 340 permits the liquid medicament to flow from the aforementioned intermediate chamber into the fill tube 322. The fill tube 322 has an end 323 that is received by the infusion device fill port. The device 314 further has a protective cap 350 that protect the fill tube 322 during device storage.

FIG. 7 shows the device 314 after the ring has received the vial 348 of liquid medicament. It may be noted the vent tube 332 is venting the vial 348 to atmospheric pressure above the liquid medicament.

Figure 8:
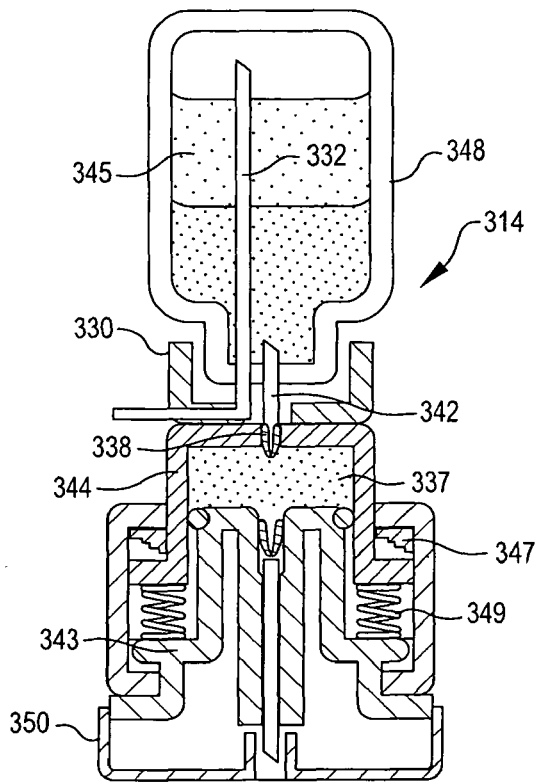
FIG. 8 is a sectional side view illustrating the apparatus of FIG. 6 after transferring a desired amount of the liquid medicament from the vial to an intermediate chamber in accordance with an embodiment of the present invention.

In FIG. 8, the plunger 344 has been withdrawn causing liquid medicament to flow from the vial 348, through transfer tube 342 and one-way valve 238, into the intermediate chamber 337 formed by the withdrawal of the plunger 344. The extent in which the plunger 344 is withdrawn and the volume of liquid medicament to be transferred, is set by spacer 347. The spacer 347 comprises two rings joined by a stepped incline. Depending upon which relative directions the rings are rotated with respect to each other, the spacer is widened or narrowed to control the travel of the plunger, and hence the volume of liquid medicament transferred to the intermediate chamber. Here, the volume so transferred is seen at 345.

Figure 9:
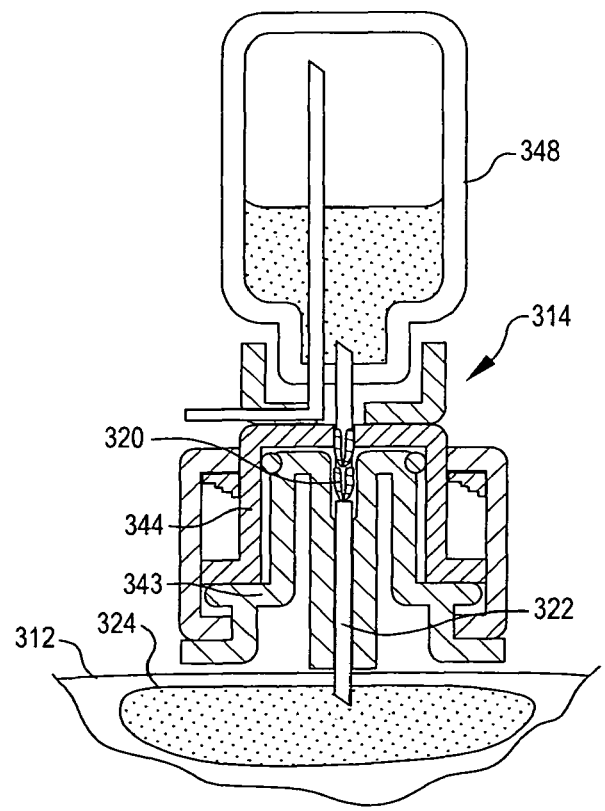
FIG. 9 is a sectional side view of the apparatus of FIG. 6 after transferring the desired amount of liquid medicament from the intermediate chamber to a reservoir of a disposable wearable infusion device according to an embodiment of the present invention.

In FIG. 9, the protective cap 350 has been removed and the filling device 314 has been coupled to an infusion device 312 for filling the reservoir 324 of the device 312. The plunger 344 has been brought to its initial position thus completely reducing the intermediate chamber. This has caused through direct positive, the liquid medicament to have flowed from the intermediate chamber, through the one-way valve 322 and fill to tube 322 into the reservoir 324 of the infusion device 312. The filling of the infusion device reservoir is now complete and the protective cover 350 may be once again placed on the filling device for storage.

While particular embodiments of the present invention have been shown and described, modifications may be made, and it is therefore intended in the appended claims to cover all such changes and modifications which fall within the true spirit and scope of the invention as defined by those claims.

What is claimed is:

1. An infusion system comprising:
   a disposable wearable infusion device having a body arranged to be adhered to a patient's skin and a reservoir for holding a liquid medicament to be infused into the patient; and
   a filler device arranged to be detachably received by the infusion device and to transfer a volume of the liquid medicament to the infusion device reservoir,
   wherein the filler device is arranged to receive a vial of the liquid medicament, wherein in the filler device further includes a chamber that receives the liquid medicament from the vial and a pumping member that displaces the liquid medicament from the chamber to the infusion device reservoir,
   wherein the pumping member is within the chamber.

2. The system of claim 1, wherein the filler device is arranged to transfer a set volume of the liquid medicament from the vial to the infusion device reservoir.

3. The system of claim 1, wherein the pumping member comprises a piston.

4. The system of claim 1, wherein the filler includes a vent that vents the liquid medicament to atmospheric pressure.

* * * * *